United States Patent
Mahajan et al.

(10) Patent No.: US 12,039,699 B2
(45) Date of Patent: Jul. 16, 2024

(54) METHOD AND SYSTEM FOR SIMULATING AND CONSTRUCTING ORIGINAL MEDICAL IMAGES FROM ONE MODALITY TO OTHER MODALITY

(71) Applicants: Vidur Mahajan, New Delhi (IN); Aravind Upadhyaya, Karnataka (IN)

(72) Inventors: Vidur Mahajan, New Delhi (IN); Aravind Upadhyaya, Karnataka (IN); Abhishek S. Venkataram, Karnataka (IN); Vasantha Kr. Venugopal, New Delhi (IN)

( * ) Notice: Subject to any disclaimer, the term of this patent is extended or adjusted under 35 U.S.C. 154(b) by 614 days.

(21) Appl. No.: 17/058,343

(22) PCT Filed: May 25, 2019

(86) PCT No.: PCT/IB2019/054356
§ 371 (c)(1),
(2) Date: Nov. 24, 2020

(87) PCT Pub. No.: WO2019/224800
PCT Pub. Date: Nov. 28, 2019

(65) Prior Publication Data
US 2021/0110520 A1 Apr. 15, 2021

(30) Foreign Application Priority Data
May 25, 2018 (IN) .............................. 201811019643

(51) Int. Cl.
| | |
|---|---|
| *G16H 30/40* | (2018.01) |
| *G06N 3/08* | (2023.01) |
| *G06T 3/14* | (2024.01) |
| *G06T 3/40* | (2006.01) |
| *G06T 5/50* | (2006.01) |
| *G06T 5/90* | (2024.01) |
| *G16H 50/50* | (2018.01) |

(52) U.S. Cl.
CPC ............... *G06T 5/50* (2013.01); *G06N 3/08* (2013.01); *G06T 3/14* (2024.01); *G06T 3/40* (2013.01); *G06T 5/90* (2024.01); *G16H 30/40* (2018.01); *G16H 50/50* (2018.01); *G06T 2207/10081* (2013.01); *G06T 2207/10088* (2013.01); *G06T 2207/10104* (2013.01); *G06T 2207/10108* (2013.01); *G06T 2207/10132* (2013.01); *G06T 2207/20084* (2013.01); *G06T 2207/30004* (2013.01)

(58) Field of Classification Search
CPC .......... G16H 50/50; G16H 30/40; G06N 3/08; G06N 3/04; G06N 3/045; G06N 3/0455; G06N 3/0464; G06N 3/0475; G06T 3/0068; G06T 3/40; G06T 5/50; G06T 5/007; G06T 2207/10081; G06T 2207/10088; G06T 2207/10104; G06T 2207/10108; G06T 2207/10132; G06T 2207/20084; G06T 2207/30004; G06T 7/0012; G06T 2210/41; G06T 2211/441; G06T 2211/464; G06T 3/14; G06T 5/60; G06T 5/90

See application file for complete search history.

(56) References Cited

U.S. PATENT DOCUMENTS

| | | | |
|---|---|---|---|
| 2008/0292194 A1* | 11/2008 | Schmidt | G06T 7/143 382/131 |
| 2009/0082637 A1* | 3/2009 | Galperin | G16H 30/20 600/300 |
| 2017/0357879 A1* | 12/2017 | Odaibo | G06N 3/044 |
| 2018/0285778 A1* | 10/2018 | Nori | G06F 18/254 |
| 2018/0336677 A1* | 11/2018 | Sloan | G01R 33/5608 |
| 2019/0005684 A1* | 1/2019 | De Fauw | G06T 11/003 |
| 2019/0104940 A1* | 4/2019 | Zhou | A61B 5/0035 |
| 2019/0192880 A1* | 6/2019 | Hibbard | G06N 3/045 |
| 2019/0206095 A1* | 7/2019 | Xing | G06T 11/003 |
| 2019/0325621 A1* | 10/2019 | Wang | G06N 3/045 |
| 2019/0362522 A1* | 11/2019 | Han | A61N 5/1039 |
| 2020/0211209 A1* | 7/2020 | Liao et al. | G06T 7/30 |
| 2020/0219262 A1* | 7/2020 | Hsiao | G06V 10/764 |
| 2020/0311914 A1* | 10/2020 | Zaharchuk | G06N 20/10 |
| 2021/0201546 A1* | 7/2021 | Andersson et al. | G06T 11/60 |
| 2022/0012881 A1* | 1/2022 | Han | A61N 5/103 |

FOREIGN PATENT DOCUMENTS

| | | |
|---|---|---|
| WO | WO 2017/223560 A1 | 12/2017 |
| WO | WO 2019/128660 A1 | 7/2019 |

OTHER PUBLICATIONS

PCT/IB2019/054356 International Search Report, dated Dec. 9, 2019.

* cited by examiner

*Primary Examiner* — Andrew W Johns
(74) *Attorney, Agent, or Firm* — SOROKER AGMON NORDMAN RIBA (57) ABSTRACT

The present invention relates to an improved method and system for simulating and constructing original actual Magnetic Resonance Images MRI from first modality of a patient to second modality, wherein the system is configured to receive an input MRI image taken in first modality, pre-process the input MRI image, send the processed image to a Convolutional Neural Network (CNN), and obtain the new constructed MRI images in second modality that are identical at the pixel level to the actual image as captured by the MRI machines.

18 Claims, 9 Drawing Sheets

FIG. 1

| Input T2 W Images 1 image is sent at a time | Network A Output 1 image as output at a time |
|---|---|
| Image 1 | → Image 1 |
| Image 2 | → Image 2 |
| Image 3 | → Image 3 |
| Image 4 | → Image 4 |
| Image 5 | → Image 5 |
| Image 6 | → Image 6 |
| Image 7 | → Image 7 |
| Image 8 | → Image 8 |
| Image 9 | → Image 9 |
| Image 10 | → Image 10 |
| Image 11 | → Image 11 |
| Image 12 | → Image 12 |
| Image 13 | → Image 13 |
| Image 14 | → Image 14 |
| Image 15 | → Image 15 |
| Image 16 | → Image 16 |
| Image 17 | → Image 17 |
| Image 18 | → Image 18 |
| Image 19 | → Image 19 |
| Image 20 | → Image 20 |
| Image 21 | → Image 21 |
| Image 22 | → Image 22 |
| Image 23 | → Image 23 |
| Image 24 | → Image 24 |
| Image 25 | → Image 25 |

METHOD AND SYSTEM FOR SIMULATING AND CONSTRUCTING ORIGINAL MEDICAL IMAGES FROM ONE MODALITY TO OTHER MODALITY

FIELD OF THE INVENTION

The present invention generally relates to automated analysis (i.e. simulating and constructing) of medical images i.e. Magnetic Resonance Images (MRI), Computed Tomography (CT) images, Ultrasound Images, Positron Emission Tomography Images, Single-Photon Emission Computed Tomography Images are the like. More particularly, the present invention relates to an improved method and system for simulating and constructing original actual Magnetic Resonance Images MRI from first modality of a patient to second modality.

BACKGROUND OF THE INVENTION

The study of the human body and its connection to human activities has been of interest to scientists for centuries. Medical imaging methods have been developed to allow a visualization of the human body in recent years. Magnetic Resonance Imaging (MRI) is such a technique that provides a noninvasive way to view the structure of the human body.

Conventional MRI scan procedure for each of a typical series like T1W, T2W, T2 Flair, T1 contrast take an average of five minutes per series acquisition or gathering a single MRI image of a patient in one modality. It is too time consuming to gather MRI images in second modality of a patient which presently require a prohibitively long duration. Over the years, a number of high-speed data acquisition techniques have been developed to address this issue. These imaging techniques are routinely used worldwide, producing critical tomographic information of the human body and enabling evaluation of not only anatomical and functional features but also cellular and molecular features in modern medicine. However, each individual imaging modality has its own contrast mechanism with strengths and weaknesses, and imaging protocols depend on many interrelated factors. Even with current multi-modality imaging various limitations exist, including reconstruction techniques that are inefficient and/or inaccurate.

There is a constant need for a method and system for simulation and constructing the medical images i.e. MRI and the like, from one modality to different modality with more accuracy, same pixel level, better throughput, lowers the cost of MRI services, helps in efficient triaging, and improves overall patient experience of MRI scanning.

SUMMARY OF THE INVENTION

The subject invention provides improved method and system for simulating and constructing actual MRI images in second modality from a source or actual MRI image of a patient taken in first modality.

One embodiment of the present invention relates to a method of simulating and constructing actual MRI images in second modality from a source MRI image of a patient taken in first modality, the method comprising the steps of: receiving an input MRI image taken in first modality, pre-processing the input MRI image, sending the processed image to a Convolutional Neural Network (CNN), and obtaining the new constructed MRI images in second modality that are identical at the pixel level to the actual image as captured by the MRI machines.

Another embodiment of the present invention relates to a system for simulating and constructing an actual MRI images in second modality from a input MRI image of a patient taken in first modality comprising: an input interface to receive the input MRI image taken in first modality; a storage device for storing the received input MRI image; a processor processed the input MRI image through the convolutional neural network, to obtain the new constructed MRI images in second modality that are identical at the pixel level to the actual image as captured by the MRI machine.

The first modality and second modality can be T1 & T2-weighted images, T2 Flair, T1 contrast, Diffusion Weighted image (DWI) or the like.

The input image and output image can be a Magnetic Resonance Imaging, Computed Tomography, ultrasound imaging, Positron Emission Tomography, and Single-Photon Emission Computed Tomography or the like.

The method further comprising the step of providing the output image as input to a Generative Adversarial Networks (GAN) that helps make the output MRI image more clear and closer to actual image as captured by the MRI machines.

Another aspect of the invention relates to system for simulating and constructing actual MRI images in second modality from a source MRI image of a patient taken in first modality.

Yet another aspect of the invention relates to an apparatus for simulating and constructing actual MRI images in second modality from a source MRI image of a patient taken in first modality.

OBJECTS OF THE INVENTION

A primary object and advantage of the present invention is to provide an improved method, and system for simulating and constructing MRI images reducing substantially the MRI exam time.

Another object and advantage of the present invention is to provide an improved method, and system for simulating and constructing actual MRI images in second modality from a source MRI image of a patient taken in first modality which normally would need to be acquired separately.

Another object and advantage of the present invention is to provide an improved method, and system for simulating and constructing actual MRI images in second modality that are identical at the pixel level to the source original MRI image of a patient taken on a MRI scanner in first modality.

Another object and advantage of the present invention is to reduce the time associated with MRI scans substantially and improve the productivity of the MRI scanner which lowers the cost of providing MRI services, helps in faster triaging and improves patient experience of MRI scanning.

Another object and advantage of the present invention is to provide an improved technique that economizes total scan time of a multi-scan MRI session while preserving, or even enhancing, the quality of the scans.

Another object and advantage of the present invention is to provide an improved technique not only to simulate and construct actual MRI images in second modality from a source original MRI image but also enhance the clarity of the constructed MRI image.

Another object and advantage of the present invention is to provide an improved technique which establishes the mathematical relationship/function between a pixel on an MRI scan to the tissue behavior as seen on an actual MRI image and provides output MRI images which is very close to the actual image with direct benefits to patients.

Another object and advantage of the present invention is to provide an improved technique which successfully recognizes patterns in images that are invisible to the human eye to help simulate and construct images which currently require separate acquisitions.

Another object and advantage of the present invention is to provide an improved technique which uses deep learning to find a function that helps in translating one MRI image to another.

BRIEF DESCRIPTION OF THE ACCOMPANYING DRAWINGS

The foregoing and other objects, features, and advantages of the invention will be apparent from the following detailed description taken in conjunction with the accompanying drawings, wherein.

DETAILED DESCRIPTION OF THE INVENTION

The following description contains specific information pertaining to implementations in the present disclosure. One skilled in the art will recognize that the present disclosure may be implemented in a manner different from that specifically discussed herein. The drawings in the present application and their accompanying detailed description are directed to merely exemplary implementations. The drawings and related description are only for purposes of illustrating the various embodiments and are not to be construed as limiting the invention. Unless noted otherwise, like or corresponding elements among the figures may be indicated by like or corresponding reference numerals.

The aspects of the present disclosure may be embodied as a system, method, apparatus and/or computer program product. Accordingly, aspects of the present disclosure may take the form of an entirely hardware embodiment, an entirely software embodiment (including firmware, resident software, micro-code, etc.), or an embodiment combining software and hardware aspects that may generally be referred to herein as a "system."

It is to be understood that the aspects of the present disclosure, as generally described herein, can be arranged, substituted, combined, separated, and designed in a wide variety of different configurations, all of which are explicitly contemplated herein.

Furthermore, aspects of the present disclosure may take the form of a computer program product embodied in one or more non-transitory computer readable medium(s) having computer readable program code encoded thereon.

Any combination of one or more non-transitory computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. In the context of this document, a computer readable storage medium may be any tangible medium that can contain or store a program for use by or in connection with an instruction execution system, apparatus or device.

Figure 1:
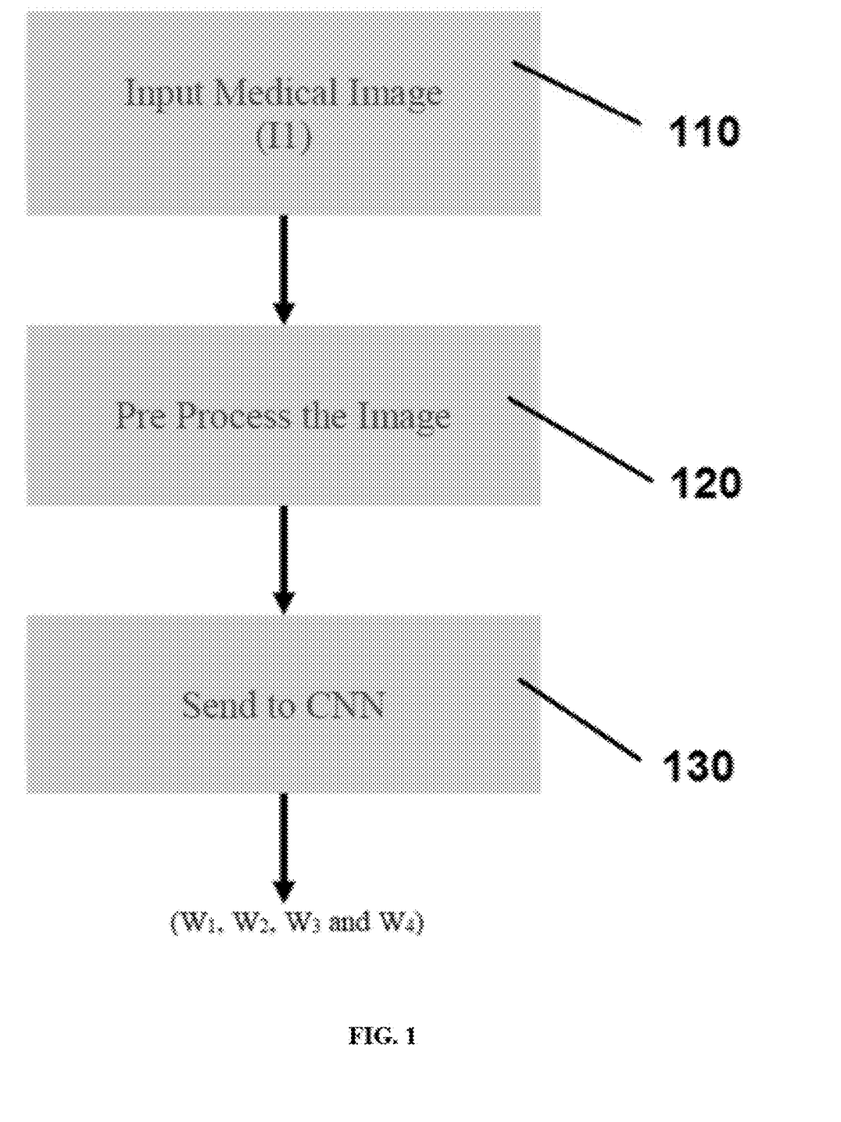
FIG. 1 illustrates a flowchart of the method of simulating and constructing actual MRI images in second modality from a source MRI image of a patient taken in first modality according to the present invention.

Referring now to FIG. 1, a flowchart of the method of simulating and constructing actual MRI images in second modality from a source MRI image of a patient taken in one modality is illustrated. The method of simulating and constructing actual MRI images in second modality from a source MRI image of a patient taken in one modality, starts at step 110 receiving an input MRI image taken in one modality, pre-processing at step 120 the input MRI image, sending at step 130 the processed image to a Convolutional Neural Network (CNN).

In pre-processing step 120 the input images undergo a sequence of processing steps for better training of the network and thus increases the efficiency and accuracy of the network. The pre-processing steps comprising the steps of registration and resampling of the input image using Euler 3D Rigid Transform algorithm, where the input image is registered and resampled to the dimensions (x, y, z)=(512, 512, 25). For example, if an input image is (512, 512, 50) then after said steps of registration and resampling of the input image we obtain the image having dimension of (512, 512, 25). We use a standard dimension, however, the dimension can be vary. The registration and resampling of the input image can be performed by different algorithm.

The Euler 3D rigid transform represents a rigid rotation in 3D space. That is, a rotation followed by a 3D translation. The rotation is specified by three angles representing rotations to be applied around the X, Y and Z axes one after another. The translation part is represented by a Vector. This transform also allows the users to set a specific center of rotation. Users can also specify the coordinates of the center of rotation.

The next step in pre-processing steps is Organ of interest extraction from the MRI scan, in present invention brain images has been used, where Brain Extraction algorithm is apply to extract just the brain from the MRI scans because the skull usually does not have any pathologies associated with it and hence rarely being used for predicting a condition in case of MRI scans. The scaling down of not usable data reduces almost 25% of the data that has to be translated. This 25% reduction in pixels helps the network to focus only on learning translation of the Brain hence increasing accuracy of the network predictions.

Scaling down is dimensionality reduction. When the input data to an algorithm is too large to be processed and it is suspected to be redundant (e.g. the same measurement in both feet and meters, or the repetitiveness of images presented as pixels), then it can be transformed into a reduced set of features. This can be performed in multiple ways. One algorithm is Registration and Resampling, and another is using a 50% scale down.

For example, if the input image is (x, y, z)=(512, 512, 80) after registration and resampling it will be scaled down to (512, 512, 25). Even this scaled down image is too big in dimensionality to be sent to Network D and hence we scale it down further by 50% to make it (256, 256, 13) to be sent to network D The next step in pre-processing steps is correction of image intensity, in present invention a bias field correction algorithm is used to correct non uniformities in image intensity which occur on the MRI image due to the high magnetic field usage.

The next step in pre-processing steps is enhancing the contrast and brightness of the image for better visibility of the different anatomical structures to highlight abnormalities. This improve quality or optimizing characteristics for maximum visibility. Mostly medical images have a wide range of pixel intensities, in present invention a histogram algorithm is used that provides a range of pixels that covers the majority of the pixel intensities in the optimal viewing range of an image thus giving us a small and precise window of pixel intensities which when applied through a Lookup Table to the MRI images will provide the most optimal view.

The step of sending 130 processed images to a Convolutional Neural Network (CNN). In present invention the convolutional neural network is a combination of four Networks (like Network A, Network B, Network C and Network D), the architecture of each Network is a combination of Variation Auto Encoder Network and Generative Adversarial Network. Each individual network's final weights will be ensembled to get the best performing final network weights.

Variation Auto Encoder Network (VAE) consists of an encoder, a decoder, and a loss function. In probability model terms, the variational autoencoder refers to approximate inference in a latent Gaussian model where the approximate posterior and model likelihood are parametrized by neural nets (the inference and generative networks). VAE is use to design complex generative models of data, and fit them to large datasets. They can generate images of fictional faces and high-resolution digital artwork.

A generative adversarial network (GAN) is a type of AI machine learning (ML) technique made up of two nets that are in competition with one another in a zero-sum game framework. GANs typically run unsupervised, teaching itself how to mimic any given distribution of data. The two neural networks that make up a GAN are referred to as the generator and the discriminator. The generator is a type of convolutional neural network that will create new instances of an object, and the discriminator is a type of deconvolutional neural network that will determine its authenticity, or whether or not it belongs in a dataset.

Both entities compete during the training process where their losses push against each other to improve behaviors, known as backpropagation. The goal of the generator is to produce passable output without being caught while the goal of the discriminator is to identify the fakes. As the double feedback loop continues, the generator produces higher-quality output and the discriminator becomes better at flagging imposters.

Figure 1A:
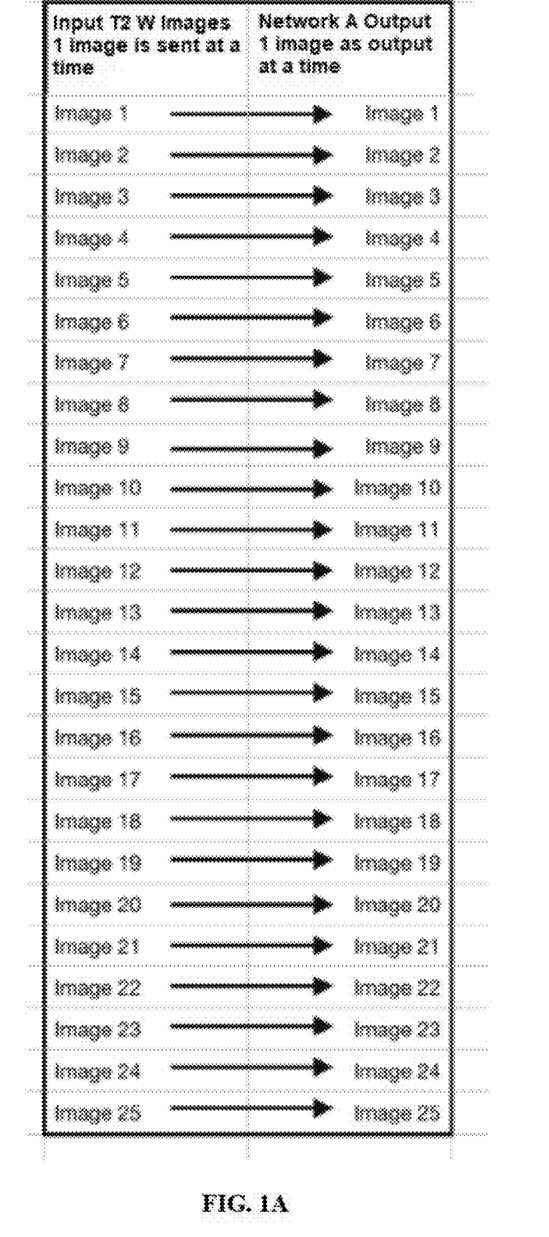
FIG. 1A illustrates a simulating and constructing actual MRI images in second modality from Network A according to the present invention.

Referring now to FIG. 1A illustrates a simulating and constructing actual MRI images in second modality from Network A according to the present invention, where only one input image at a time is passed across the network A which generate one output image which is in different modality.

Figure 1B:
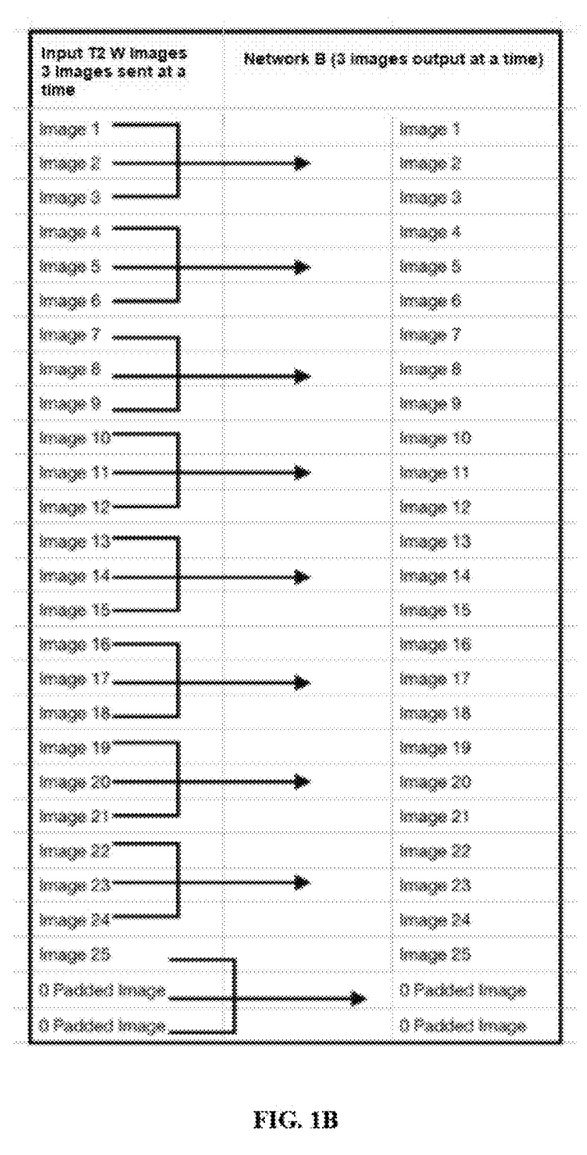
FIG. 1B illustrates a simulating and constructing actual MRI images in second modality from Network B according to the present invention.

Referring now to FIG. 1B illustrates a simulating and constructing actual MRI images in second modality from Network B according to the present invention, where a Lambda which is a hardware constraint and a graphics card is use which define the number of images passes through the Network B. However, lambda can increase according to the quality of the graphics card.

Figure 1C:
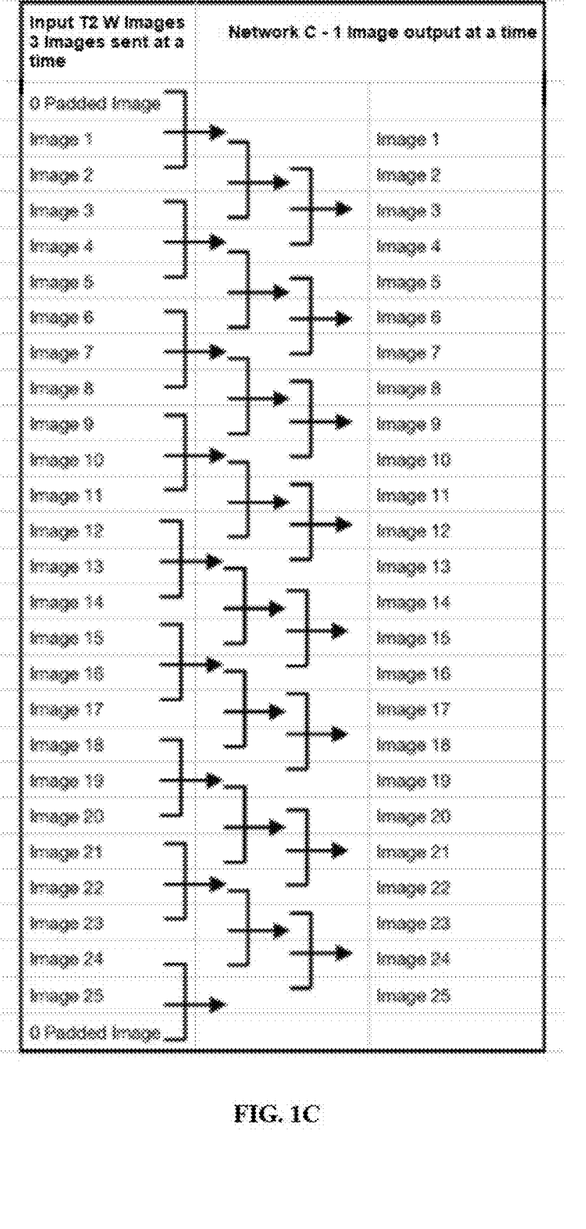
FIG. 1C illustrates a simulating and constructing actual MRI images in second modality from Network C according to the present invention.
Figure 1D:
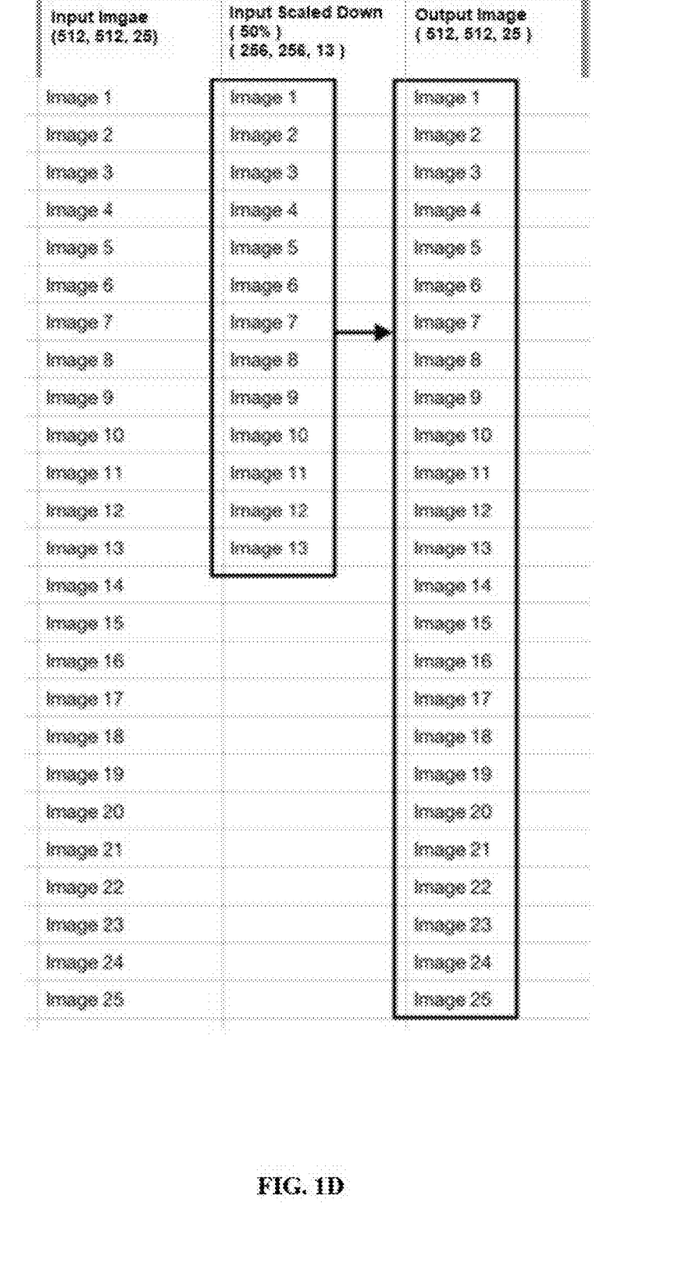
FIG. 1D illustrates a simulating and constructing actual MRI images in second modality from Network D according to the present invention.

In present invention the value of lambda-03, where three number of images are passed to the network B at a time for learning and the network output is lambda number of slices. So instead of one image going into the network and predicting one image, 3 images as per the sequence are sent to the network and the 3 images are predicted as well. If a factor of lambda number of slices are not available then an image that is 0 padded is sent. That is if the input sequence is of 25 images, a factor of 3 images being sent for every iteration, the last iteration 8th iteration will just be left 1 image as input. In this case 2, other 0 padded images are sent along to qualify the lambda. There are no overlaps when images are sent that is if input sequence is of 25 images then the first iteration will send image #1, image #2 and image #3 to the network, the second iteration will send image #4, image #5, image #6 to the network and so on as a factor of the lambda Referring now to FIG. 1C illustrates a simulating and constructing actual MRI images in second modality from Network C according to the present invention; here, (Lambda=3) lambda number of images are passed to the network C for learning and predicting 1 single image. So, network C passes 3 images at a time from the sequence as input and predicts just 1 image as output. Network C predict the middle image from the three input images, predicted image is dependent on the previous image and post image of the predicted image.

Referring now to FIG. 1D illustrates a simulating and constructing actual MRI images in second modality from Network D according to the present invention, here the input is the entire 3D stack of images. That is all the 25 images are sent in 1 iteration to the network and the output of all 25 slices is predicted in 1 iteration itself. The 3D stack is scaled down by 50% that is a (512, 512, 25) will be scaled down to (256, 256, 13). The scaled down is hardware dependent which can be minimize according to the graphic cards which assembled.

Figure 2:
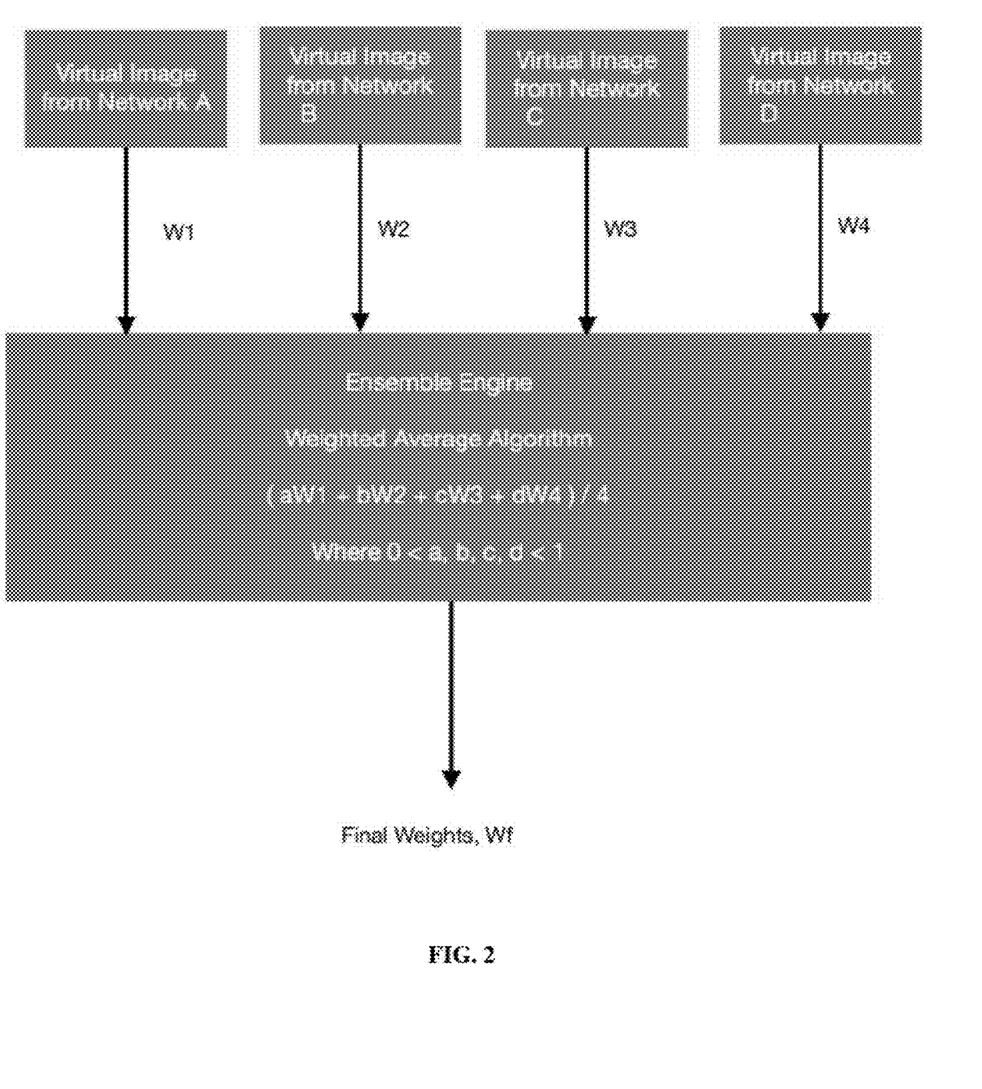
FIG. 2 illustrates an Ensemble Engine to process the output that is the network weights generated by combination of Convolutional neural Networks according to the present invention.

Referring now to FIG. 2 an Ensemble Engine to process the output image processed from the Convolutional neural Network is illustrated. The Ensemble Engine receive the output image from the Convolutional Neural Network A, B, C and D respectively. The received output image is processed by the Ensemble Engine which perform weighted average algorithm to achieve the final weight $W_f$ which is the best possible weight for higher prediction accuracy of virtual images.

Figure 3:
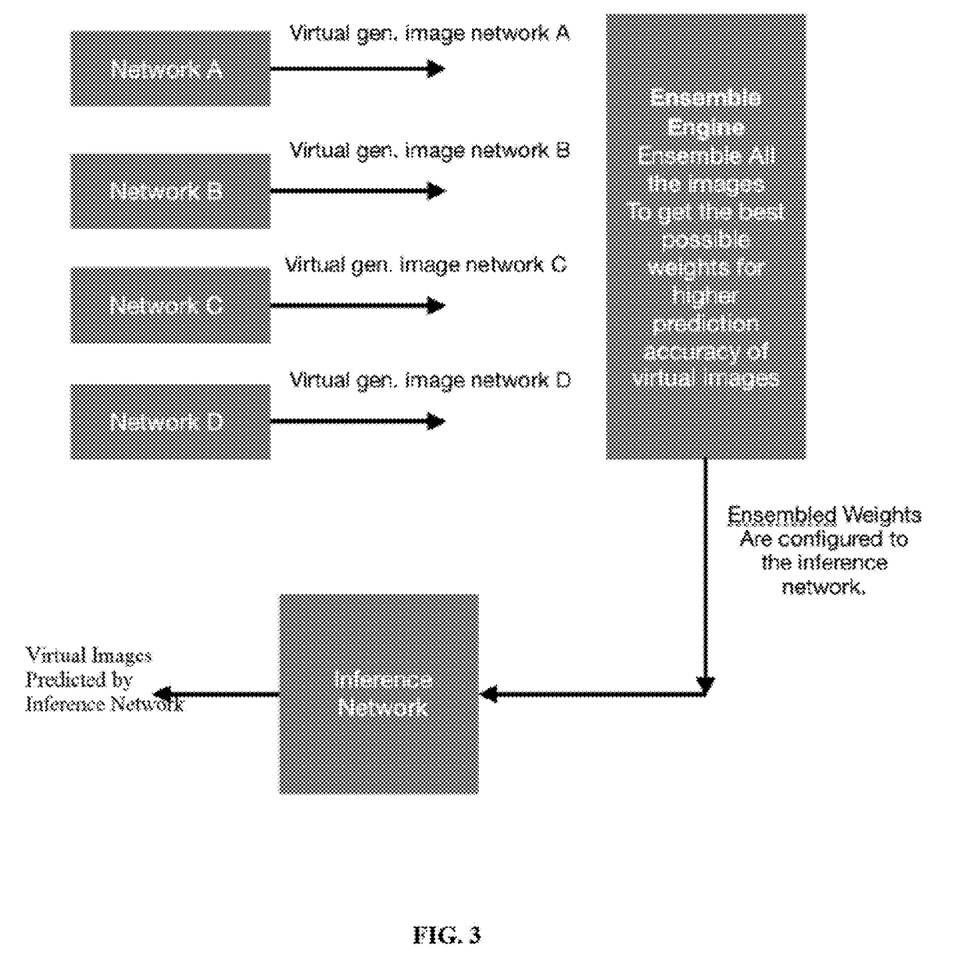
FIG. 3 illustrates an Inference Network to process the input image to predict the output image by using the network weights from the Ensemble Engine according to the present invention.

Referring to FIG. 3 an Inference Network to process the output image processed from the Ensemble Engine is illustrated; it is a neural network that is use for predictions at the client site/research site for producing virtual images of a specific modality from the prescribed input images modality without the backward propagation. The weights ($W_1$, $W_2$, $W_3$ and $W_4$) getting from Network A, B, C and D respectively passed through the ensemble engine which calculate the best weights for the inference network that will give the highest accuracy of virtually generated images. The inference network generates the new constructed MRI images in second modality that are identical at the pixel level to the actual image as captured by the MRI machines.

Figure 4:
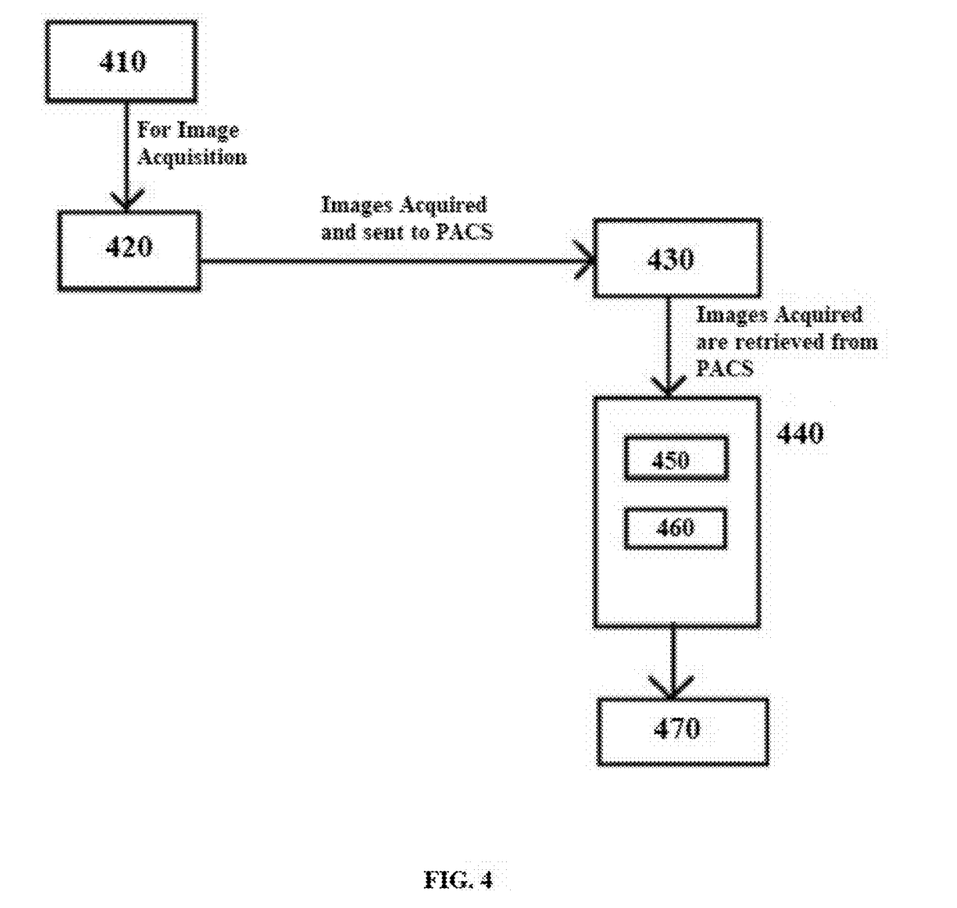
FIG. 4 illustrates a System simulating and constructing actual MRI images in second modality from a source MRI image of a patient taken in first modality according to the present invention.

FIG. 4 illustrates a System simulating and constructing actual MRI images in second modality from a source MRI image of a patient 410 taken in one modality according to the present invention. The system comprising an MRI Machine 420 which scan the organ of the patient, the scanned images are acquire and send to the Picture Archiving and Communication System (PACS) which act as a storage unit 430, however different types of storage unit we can use according to the type of images scan through the MRI Machine. The client accesses the saved images through the client system 440 through an application. The client system comprises a CPU (central processing unit) 450 and GPU (graphical processing unit) 460. Client select the appropriate input image in first modality and the client system will generate virtual image in second modality. The input image modality must be specify through the application. Virtual image of the desired modality is saved as DICOM (digital imaging and communication in medicine) and viewed at any DICOM viewer. The client system comprises GPU includes a graphics card that support the AI (artificial intelligence) library and CPU. However, the GPU and CPU select according to the type of medical image which need to be processed and the requirement of the client. The client includes hospitals, researchers or the like. The system includes cloud server 470 which configure to provide levels of performance, security and control in a shared "virtualized" environment that's managed by your cloud hosting provider.

Figure 5:
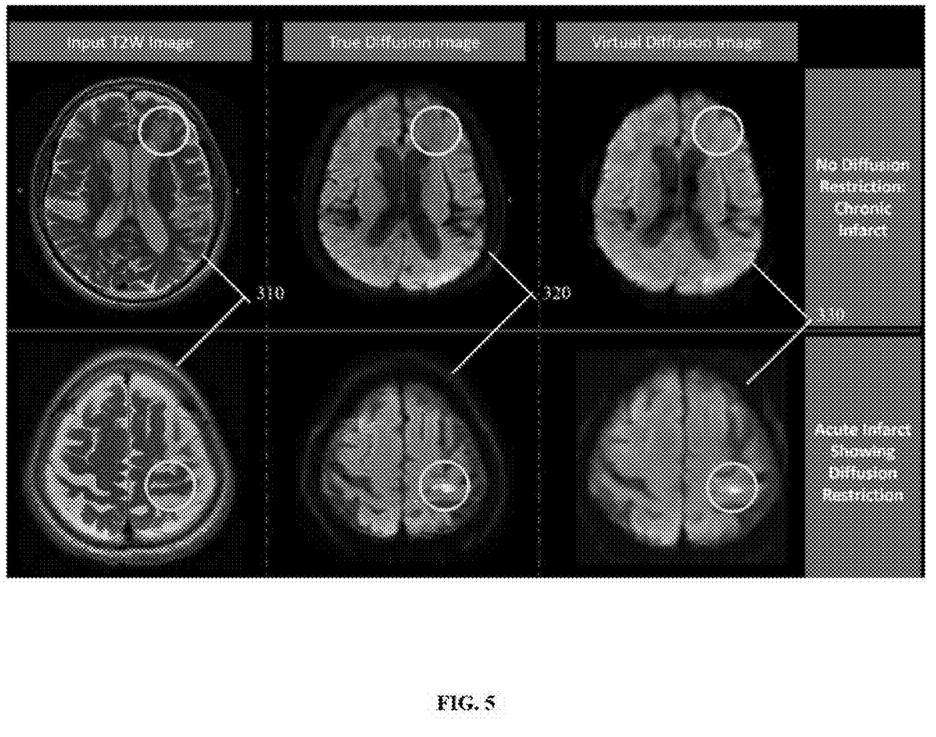
FIG. 5 illustrates simulated and constructed actual MRI images in second modality from a source MRI image of a patient taken in first modality according to the present invention.

Referring now to FIG. 5, it illustrates the simulated and constructed actual MRI images in second modality from a source MRI image of a patient taken in one modality according to the present invention. The input T2 Weighted Image (T2WI) image 310 is an actual original image of a patient taken in one modality. True Diffusion Image 320 is a real diffusion image acquired from said patient. The constructed Diffusion Image 330 is the image which has been simulated and constructed by the system and method of the current invention. A diffusion image is needed to check if a brain infarct (stroke) is acute or chronic. In case of acute strokes, there is a bright spot and in case of chronic, there is no change in diffusion images. The reason a separate diffusion image is taken because radiologists are unable to differentiate between acute and chronic infarcts on a T2WI. Thus, it can be understood that the current method of the invention prevents the need of performing and acquiring a real diffusion image 320.

To further explain the improved method of the invention, the convolutional layers, maxpooling and upsampling layers are used together to collect features from an input MRI image, for example a T2 weighted image (T2WI). The maxpooling and upsampling process are explained below:

Max pooling is a sample-based discretization process. The objective is to down-sample an input representation (image, hidden-layer output matrix, etc.), reducing its dimensionality and allowing for assumptions to be made about features contained in the sub-regions binned. This is done to in part to help over-fitting by providing an abstracted form of the representation. As well, it reduces the computational cost by reducing the number of parameters to learn and provides basic translation invariance to the internal representation. Max pooling is done by applying a max filter to (usually) non-overlapping subregions of the initial representation.

Upsampling is the process of inserting zero-valued samples between original samples to increase the sampling rate. (This is sometimes called "zero-stuffing".) This kind of upsampling adds undesired spectral images to the original signal, which are centered on multiples of the original sampling rate. "Interpolation", in the DSP sense, of the process follows the upsampling by filtering. (The filtering removes the undesired spectral images.) As a linear process, the DSP sense of interpolation is somewhat different from the "math" sense of interpolation, but the result is conceptually similar: to create "in-between" samples from the original samples. The result is as if you had just originally sampled your signal at the higher rate.

Further, these features are processed through a Convolutional Neural Network (CNN) to generate new output MRI images, which are, not being limited to, a T1 weighted image (T1WI) and a Diffusion Weighted image (DWI) that are identical at the pixel level to the image as captured by the MRI machines. The T1 weighted image (T1WI), T2 weighted image and a Diffusion Weighted image (DWI) are explained below:

T1W—T1-weighted images are produced by using short TE and TR times. The contrast and brightness of the image are predominately determined by T1 properties of tissue. Repetition Time (TR) is the amount of time between successive pulse sequences applied to the same slice. Time to Echo (TE) is the time between the delivery of the RF pulse and the receipt of the echo signal.

T2W—T2-weighted images are produced by using longer TE and TR times. In these images, the contrast and brightness are predominately determined by the T2 properties of tissue.

Diffusion weighted imaging (DWI) is designed to detect the random movements of water protons. Water molecules diffuse relatively freely in the extracellular space; their movement is significantly restricted in the intracellular space. Spontaneous movements, referred to as diffusion, rapidly become restricted in ischemic brain tissue. During ischemia, the sodium-potassium pump shuts down and sodium accumulates intracellularly. Water then shifts from the extracellular to the intracellular space due to the osmotic gradient. As water movement becomes restricted intracellularly, this results in an extremely bright signal on DWI. Thus, DWI is an extremely sensitive method for detecting acute stroke.

The present disclosure comprises 15 layers which are divided into 5 down layers and 10 up layers used in the convolution neural network (CNN). The CNN comprises two parts i.e. an encoder and a decoder. The encoder collects the features from the input image and keeps reducing the spatial dimensions of the input image. This happens all the way till a high enough z depth is created and the spatial size of the input image is reduced to a small enough size so that computation is easy. Once this is achieved then the features are upsampled and concatenated with the residual connection from the encoder end and convolved further to get the output from the decoder end.

The method may further include the step of aggregating the current MRI image data with the plurality of prior MRI image data for use in constructing a subsequent MRI image.

Current and prior MRI image data may include two-dimensional, three-dimensional or four-dimensional data.

The present concept of virtual image generation is not restricted to brain organ, the present concept can be applied to other body organs as well.

Although, the present invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the scope of the invention as set forth in the claims.

Accordingly, it is not intended that the scope of the foregoing description be limited to the exact description set forth above, but rather that such description be construed as encompassing such features that reside in the present invention, including all the features and embodiments that would be treated as equivalents thereof by those skilled in the relevant art.

Thus, it is intended that the scope of the present invention herein disclosed should not be limited by the particular disclosed embodiments described above but should be determined only by a fair reading of the complete specification to follow in this case.

The invention claimed is:

1. A method of simulating and constructing an actual images in second modality from an input image of a patient taken in a first modality, the method comprising the steps of:
   receiving the input image taken in first modality;
   pre-processing the input image;
   sending the pre-processed image to a Convolutional Neural Network (CNN), wherein the Convolutional Neural Network (CNN) comprises a combination of four or more networks comprising at least a Network A, a Network B, a Network C and a Network D,
   wherein design of each network is a combination of a Variation Auto Encoder Network (VAN) and a Generative Adversarial Network (GAN);
      obtaining a new constructed image being an output image in a second modality from the pre-processed input image that are identical at the pixel level to an actual image as captured by a machine.

2. The method as claimed in claim 1, wherein the first modality and second modality comprise T1 & T2-weighted images, T2 Flair, T1 contrast, Diffusion Weighted image (DWI).

3. The method as claimed in claim 1, wherein the input, image and output image comprise a Magnetic Resonance Imaging, Computed Tomography, ultrasound imaging, Positron Emission Tomography, and Single-Photon Emission Computed Tomography.

4. The method as claimed in claim 1, wherein preprocessing the input image comprising the steps of:
   registering and resampling of the input image into 3 dimensions (x, y, z);
   extracting not usable data from the image to reduce pixels of the not usable data;
   correcting non uniformities in image intensity; and
   enhancing the contrast and brightness of the image for better visibility of the different anatomical structures to highlight abnormalities.

5. The method as claimed in claim 1, wherein the Network A configured to pass one input image in the first modality at a time and generate one output image in the second modality.

6. The method as claimed in claim 1, wherein Network B configured to pass $\lambda$ no. of the input image in first modality at a time and generate $\lambda$ no. of the output image in second modality, wherein the $\lambda$ is a hardware constraint.

7. The method as claimed in claim 1, wherein Network C configured to predict a middle image from the input image, where the prediction of image dependent on the previous image and post image of the predicted image.

8. The method as claimed in claim 1, wherein Network D configured to predict a middle image from the input image, where the prediction of image dependent on the previous image and post image of the predicted image.

9. The method as claimed in claim 1, wherein obtaining the new constructed images in second modality that are identical at the pixel level to the actual image as captured by the machine further comprising the steps of:
   receiving weights (W1, W2, W3 and W4) getting from Network A, B, C and D respectively;
   weighted averaging of the images from the CNN network to achieve a final weight Wf to predict accuracy of virtual images; and
   processing the final weight Wf to an inference network to generate a new constructed image in second modality that are identical at the pixel level to the actual image as captured by the machines.

10. A system for simulating and constructing an actual images in second modality from an input image of a patient taken in first modality comprising:
    an input interface to receive the input image taken in first modality;
    a storage device for storing the received input image;
    a processor to pre-process the input image through a convolutional neural network wherein the Convolutional Neural Network (CNN) comprise a combination of four or more networks comprising of at least a Network A, a Network B, a Network C and a Network D;
    wherein design of each network is a combination of a Variation Auto Encoder Network (VAN) and a Generative Adversarial Network (GAN), to obtain a new constructed image in second modality from the pre-processed input image that are identical at the pixel level to an actual image as captured by a machine.

11. The system as claimed in claim 10, wherein the first modality and the second modality comprise T1 & T2-weighted images, T2 Flair, T1 contrast, Diffusion Weighted image (DWI).

12. The system as claimed in claim 10, wherein the input image and output image comprise a Magnetic Resonance Imaging, Computed Tomography, ultrasound imaging, Positron Emission Tomography, and Single-Photon Emission Computed Tomography.

13. The system as claimed in claim 10, wherein the processor is configured to:
    register and resample of the input image into 3 dimensions (x, y, z);
    extract not usable data from the image to reduce pixels of the not usable data;
    correct non uniformities in image intensity; and
    enhance the contrast and brightness of the image for better visibility of the different anatomical structures to highlight abnormalities.

14. The system as claimed in claim 10, wherein the Network A is configured to pass one input image in first modality at a time and generate one output image in second modality.

15. The system as claimed in claim 10, wherein the Network B is configured to pass λ no. of input image in first modality at a time and generate λ no. of output image in second modality, wherein the λ is a hardware constraint.

16. The system as claimed in claim 10, wherein the Network C is configured to predict a middle image from the input image, where the prediction of image dependent on the previous image and post image of the predicted image.

17. The system as claimed in claim 10, wherein the Network D is configured to predict a middle image from the input image, where the prediction of image dependent on the previous image and post image of the predicted image.

18. The system as claimed in claim 10, wherein ensembled engine obtain the new constructed images in the second modality that are identical at the pixel level to the actual image as captured by the machine further comprising the steps of:
   receive weights (W1, W2, W3 and W4) of the image getting from Network A, B, C and D respectively;
   determine weighted average of the images from the CNN network to achieve a final weight Wf to predict accuracy of virtual images; and
   process the final weight Wf to an inference network to generate the new constructed images in second modality that are identical at the pixel level to the actual image as captured by the machines.

* * * * *